United States Patent [19]

Hecht et al.

[11] 4,039,662

[45] Aug. 2, 1977

[54] OPHTHALMIC SOLUTION

[75] Inventors: Gerald Hecht; Charles D. Shively, both of Fort Worth, Tex.

[73] Assignee: Alcon Laboratories, Inc., Fort Worth, Tex.

[21] Appl. No.: 637,608

[22] Filed: Dec. 4, 1975

[51] Int. Cl.² .................. A61K 31/70; A61K 31/715
[52] U.S. Cl. ........................................ 424/180; 536/1; 536/112
[58] Field of Search ............... 260/209 D, 209 R; 424/180; 536/1, 112

[56] References Cited

U.S. PATENT DOCUMENTS 2,853,414  9/1958  Wimmer .................. 260/209 R

OTHER PUBLICATIONS

Keilich et al., "Chem. Abst.," vol. 77, 1972, p. 165009n.
Keith et al., "Chem. Abst.," vol. 83, 1975, p. 173192f.

*Primary Examiner*—Johnnie R. Brown
*Attorney, Agent, or Firm*—Fitch, Even, Tabin & Luedeka

[57] ABSTRACT

Ophthalmic solution suitable as an artificial tear material of low viscosity containing a polysaccharide and benzalkonium chloride.

8 Claims, No Drawings

OPHTHALMIC SOLUTION

The present invention relates generally to an ophthalmic solution which is suitable for general use in the eyes of humans and domestic animals. More particularly, the present invention relates to the provision of a synthetic mucous solution which has the capability of becoming adsorbed to the cornea. The ophthalmic solution of the present invention may serve as an artificial tear material useful for the treatment of patients lacking adequate natural tear substance or components, a syndrome commonly referred to as "dry eye." The ophthalmic solution is also useful as a lubricating and cushioning agent for the eye after traumatic injury or surgery. It may also be used as a corneal wetting solution for use with hard contact lenses, and in various eye irritation disorders.

Ophthalmic solutions for treatment of the eye are well known, including solutions for treating dry eye syndrome. It is known to use various polymers in ophthalmic solutions to increase their effectiveness. For example, U.S. Pat. No. 3,767,788, to Rankin, discloses an ophthalmic solution for treating dry eye syndrome containing polyethylene oxide, optionally containing polyethylene glycol, and optionally containing biocides. The Rankin patent discloses the use of biocides such as thimerosal (sodium ethylmercurithiosalicylate) and the di-, tri-, or tetrasodium ethylene diamine tetracetates. U.S. Pat. No. 3,907,985, to Rankin, discloses an ophthalmic solution for treating dry eye syndrome containing polystyrene sulfonate, and optionally polyethylene glycol.

Generally, the use of a polymer in an ophthalmic solution has been for the purpose of increasing the viscosity of the ophthalmic solution. It has been thought that increased viscosity would prolong the retention of the ophthalmic solution in the eye and increase effectiveness of the ophthalmic solution. Also, it has been thought that increased viscosity in an ophthalmic solution is desirable to provide a cushioning effect when the ophthalmic solution is used in conjunction with hard or gel-type contact lenses or to alleviate discomfort from traumatic injury or surgery. In accordance with the present invention it has been discovered that low viscosity ophthalmic solutions can be provided which adhere or bind to the corneal surface and, as a result thereof, are retained on the surface of the cornea for extended periods of time.

Accordingly, it is an object of the present invention to provide an ophthalmic solution suitable for general use in the eye of both humans and domestic animals. Another object of the present invention is to provide ophthalmic solutions which can be used as an artificial tear or mucin. It is a further object of the present invention to provide an ophthalmic solution which serves as an artificial tear for the treatment of the various conditions known as dry eye. It is a further object of the present invention to provide an ophthalmic solution which serves as an artificial tear for the treatment of keratoconjunctivitis sicca. It is a still further object of the present invention to provide an ophthalmic solution which serves as a nonviscous or low viscosity ophthalmic solution retained in the eye through adherence to the corneal surface. Yet another object is to provide an ophthalmic solution which serves to alleviate minor irritation associated with the wearing of hard contact lenses.

These and other objects of the present invention will become more apparent from the following detailed description and the accompanying claims.

In general, the present invention is directed to an ophthalmic solution which is an aqueous solution of a particular polysaccharide and benzalkonium chloride. Preferably the ophthalmic solution also includes monovalent cation containing salts at a level sufficient to make the solution isotonic, and is free from divalent cation salts which appear to interfere with the adsorptive phenomenon and subsequent tear film stabilizatin. The balance of the ophthalmic solution is water. The ophthalmic solution of the invention is particularly suitable for use as a tear substitute.

The polysaccharide is present in the ophthalmic solution at a level of from about 0.001% to about 5%, preferably from about 0.01% to about 2%. Benzalkonium chloride is present in the ophthalmic solution at a level of from about 0.001% to about 0.1% by weight, preferably from about 0.004% to about 0.02% by weight.

The particular polysaccharides useful in the ophthalmic solutions of the present invention are selected from dextrans and arabinogalactans. Dextrans are branched glucose polysaccharides synthesized by bacteria from sucrose solutions. Dextrans are primarily produced by bacteria belonging to the genera of Leuconostoc, Streptococcus, and Acetobacter. Dextrans are similar to glycogen and amylopectin, but differ therefrom in that the principle linkage between the anhydroglucose units of dextran is of the 1,6 type whereas those of glycogen and amylopectin are of the 1,4 or 1,3 type. Dextrans are commercially available and are sold in various molecular weight ranges. Dextrans useful in the ophthalmic solutions of the present invention have a molecular weight in the range of from about 10,000 to about 1,000,000 and preferably from about 20,000 to about 200,000.

Arabinogalactans useful in the present invention are wood sugars extracted from the larch tree, and are also known as larch gum. Arabinogalactans are complex, highly branched polymers of arabinose and galactose in the ratio of from about 1:3 to about 1:10. Arabinogalactans useful in the ophthalmic solutions of the present invention have a molecular weight in the range of from 10,000 to about 250,000, and are commercially available under the tradename, Stractan.

Benzalkonium chloride is the common name used to define monoalkyl dimethyl benzyl ammonium chloride compounds of the general formula $[C_6H_5CH_2N(CH_3)_2R]^+Cl^-$ where R is a mixture of alkyl groups containing 8 to 18 carbon atoms. U.S.P. benzalkonium chloride contains a particular blend of alkyl radicals. As used herein, the term benzalkonium chloride is intended to include any benzyl quaternary ammonium compound containing one or two $C_8$-$C_{18}$ long chain alkyl radicals.

The incorporation of benzalkonium chloride in various ophthalmic solutions as a biocide is known. It has been discovered, however, that benzalkonium chloride is a critical component in the present ophthalmic solution in that it combines and/or complexes in some fashion with the polysaccharides and causes the polysaccharide to remain adsorbed to the surface of the cornea and to stabilize the precorneal tear film. Thus, the use of the particular polysaccharides in combination with benzalkonium chloride in the ophthalmic solutions of the present invention results in a desired adsorption to the cornea. The presence of the benzalkonium chloride causes the polysaccharides to adhere and remain adhered to the surface of the cornea, and the polysaccharides apparently reduced the destabilizing tendency of benzalkonium chloride on the normal precorneal tearfilm.

It is known that the corneal surface is hydrophobic. Natural tears contain mucin which becomes adsorbed to the corneal surface so as to render the surface hydrophilic and thereby compatible with the aqueous components of the tearfilm. The particular polysaccharides useful in the present invention by themselves are not capable of becoming adsorbed to the cornea and therefore cannot render the cornea hydrophilic over any extended period of time. Benzalkonium chloride is known to adsorb to the cornea. However, benzalkonium chloride may have a deleterious effect on tearfilm stability, as described hereinafter, due to its highly surface active character, resulting in destabilization of the precorneal tearfilm.

It is believed that the particular polysaccharides utilized in this invention combine in solution with the benzalkonium chloride through electrostatic attraction to form a complex or aggregate of a macromolecular nature which has a desired electron charge distribution which cause the macromolecule to be adsorbed to the corneal surface and at the same time render the corneal surface hydrophilic and, therefore, compatible with the aqueous phase of the solution and the natural tear film. The macromolecule is believed to adsorb at the corneal interface through multiple points of physical adsorption which results in extended retention in the eye. The macromolecules, through their capability to adsorb at multiple sites are less likely to desorb than smaller molecules not possessing sufficient numbers of adsorption sites. Once this macromolecular complex has adsorbed at the hydrophobic ocular surface, the ocular surface becomes hydrophilic in nature and, therefore, wettable by the aqueous phase of the tearfilm.

As reported in *Investigative Ophthalmology*, March, 1975, by M. Lemp, et. al., various techniques have been utilized for examination of solution retention time in the eye. If normal blinking is prevented, the precorneal tearfilm will breakup and develop random dry spots. The interval between the last complete blink and the appearance of the first dry spot, referred to as tearfilm breakup time (BUT), has been found to be abnormally rapid in dry eye syndrome and is a reflection of decreased tearfilm stability. Normal tear film BUT is reported as 15-25 seconds with those patients tested and if upon addition of a potential artificial tear to the eye the BUT is lengthened, this lengthened BUT is interpreted as a reflection of enhanced tearfilm stability. Furthermore, if this effect of lengthened BUT can be seen over an extended duration of time, this is an indication that there is good adsorption of the ophthalmic solution to the cornea. If the tearfilm BUT is initially improved, but this improvement diminishes rapidly with time, this is an indication that the ophthalmic solution is not sufficiently adsorbed to the cornea.

The polysaccharides of the present invention are present in the ophthalmic solution at a level of from about 0.001% to about 5% by weight. At this level of use, the ophthalmic solutions generally have a viscosity in the range of from about 1 cps to about 25 cps at 25° C. The viscosity of the ophthalmic solutions are measured on a Wells-Brookfield Microviscometer (cone and plate) Model LVT. The ophthalmic solutions of the present invention do not exhibit any gel-like properties and the viscosity is low compared to other polymer-containing ophthalmic solutions which have been developed for artificial tear usage. However, the viscosity can be adjusted within the indicated range by inclusion of water soluble viscosity building agents. Suitable viscosity building agents include natural gums, such as guar gum and gum tragacanth; gelatin; starch derivatives; polymeric glycols; and cellulosic polymers, such as hydroxyethylcellulose, hydroxypropylcellulose, methylcellulose, hydroxypropylmethylcellulose, and carboxymethylcellulose. Viscosity building agents, when used, are present in the ophthalmic solutions of the invention at a level of from about 0.001% to about 1.0% by weight. The exact percentage depends on the molecular weight of the polymer used which is within the skill of the art. When a viscosity building agent is utilized, the viscosity of the ophthalmic solution may be between about 1 cps and about 25 cps, preferably between about 3 cps and about 15 cps.

For most purposes, the benzalkonium chloride present in the ophthalmic solution provides the desired biocidal preservative effect. However, additional biocides may be incorporated, if desired. For example, it is generally desirable to incorporate a suitable chelating agent to enhance the preservative effect of the benzalkonium chloride. Suitable chelating agents include di-, tri-, or tetrasodium ethylene diamine tetracetate, also known as edetates, with disodium edetate being a preferred ingredient. Other biocides that may be optionally included in the ophthalmic solution include thimerosal, phenylmercuric nitrate, chlorobutanol, and sorbic acid.

For most ophthalmic uses it is desirable that the ophthalmic solution be isotonic. Conventionally, ophthalmic solutions are rendered isotonic by addition of suitable salts, for example, sodium chloride, potassium chloride, calcium chloride, magnesium chloride, and various nitrates, citrates, acetates, etc. Heretofore, the selection of the particular salts were not considered to be of consequence, and particularly the selection of monovalent or divalent salts was not considered to be of importance. Contrary to usual practice, it has been discovered that the particular salts used to render the ophthalmic solution of the present invention isotonic are critical, and in order to provide the desired adsorption to the cornea, as evidenced by tearfilm stability, the solution must be essentially free of divalent cations. Tearfilm breakup time studies, as described herein, on solutions containing divalent cations, i.e., calcium chloride, magnesium chloride, result in inferior tearfilm stability and lack of retention of the solution on the cornea. However, identical solutions free of divalent cations show enhanced tearfilm stability and this positive effect was retained over extended periods of time. Accordingly, the salts used to establish an isotonic condition should be monovalent, i.e., sodium chloride, potassium chloride, or mixtures thereof. Generally, the monovalent salts are added in an amount sufficient to give a freezing point depression or osmotic pressure equivalent to that provided by 0.5% to 1.5% sodium chloride.

In addition to the usefulness of the ophthalmic solutions of the present invention as tearfilm substitutes, the ophthalmic solutions have usefulness as carriers for ophthalmic medications, for example: mydriatics such as tropicamide, atropine, and epinephrine; miotics such as pilocarpine and carbachol; cycloplegics such as cyclopentolate; anti-inflammatories such as dexamethasone and prednisolone; anti-infectives such as sulfas and antibiotics; and vascoconstrictors such as phenylephrine and naphazoline. The medications may be present in the form of their pharmaceutically acceptable salts or esters.

If desired, the ophthalmic solutions of the invention may be adjusted in pH by one or more of the acids or bases known for use in ophthalmic solutions. The ophthalmic solutions may be maintained in an acidic, basic, or neutral condition by use of buffers commonly employed in ophthalmic solutions. The use of suitable acids, bases, and buffering systems to establish a pH within the range of from about 3.0 to about 8.5 is well known and requires no further description. Typically, the pH of the ophthalmic solutions described herein is between about 5.0 and 8.0, preferably between about 6.0 and about 7.5.

The following examples further illustrate various features of the invention but are not intended to in any way limit the scope of the invention which is defined in the appended claims.

EXAMPLE I

Seven ophthalmic solutions having polysaccharides in accordance with the invention were prepared having the formulations set forth below in Table I. Formulations 1 and 2 did not have benzalkonium chloride. Other ophthalmic solutions were prepared in accordance with known formulations and contain polymers other than the polysacchrides of the present invention. These formulations are set forth below in Table II.

TABLE I

| Formulation Ingredient | Formulation No. Percent w/v | | | | | | |
|---|---|---|---|---|---|---|---|
| | 1 | 2 | 3 | 4 | 5 | 6 | 7 |
| Dextran | 0.5[1] | — | 0.5[1] | — | 0.1[1] | — | 0.1[2] |
| Arabinogalactan[3] | — | 0.5 | — | 0.5 | — | 0.1 | — |
| Benzalkonium chloride | — | — | 0.01 | 0.01 | 0.01 | 0.01 | 0.01 |
| Disodium ethylene diamine tetracetate | — | — | — | — | — | — | 0.05 |
| Sodium chloride | 0.9 | 0.9 | 0.9 | 0.9 | 0.9 | 0.9 | 0.8 |
| Potassium chloride | — | — | — | — | — | — | 0.1 |
| Water | qs | qs | qs | qs | qs | qs | qs |

[1] Molecular weight of 200,000
[2] Molecular weight of 70,000
[3] Commercially available under the tradename STRACTAN from Stein Hall Company

TABLE II

| Formulation Ingredient | Formulation No. Percent w/v | | | | |
|---|---|---|---|---|---|
| | 8 | 9 | 10 | 11 | 12 |
| Polyethylene glycol[1] | 0.1 | 0.1 | — | — | — |
| Polyethylene oxide[2] | — | — | 0.1 | 0.1 | 0.5 |
| Polyvinyl alcohol | — | — | 2.0 | 2.0 | — |
| Benzalkonium chloride | 0.01 | — | — | 0.01 | 0.01 |
| Thimerosal | — | 0.01 | — | — | — |
| NaCl | 0.9 | 0.9 | 0.9 | 0.9 | 0.9 |
| Water | qs | qs | qs | qs | qs |

[1] Carbowax 4000 from Carbide and Carbon Chemicals Company
[2] Polyox WSR 301 from Union Carbide Company A method has been developed for measuring absorption of polymers in solution to corneal surfaces. The adsorptive properties of ophthalmic solutions and mucin can be determined by this method. The method involves the preparation of rabbit corneal mounts and the measurement of contact angles of a drop of saline on the surface of the corneal mounts under various conditions. The method is reported in *Arch. Ophthalmol.*, Vol. 93, p. 134, Feb. 1975 by Lemp, et al.

In the method, freshly enucleated eyes from rabbits are used. Within 30 minutes of enucleation, the eyes are placed in inverted screw-type bottle caps with an 11 mm central hole with the cornea protruding from the hole. Liquid paraffin is poured over the posterior aspect of the eye until the cap is filled. The paraffin is cooled and after the paraffin has hardened, the the entire solid paraffin globe mount can be unscrewed and removed from the screw cap. The resultant cornea-paraffin block provides a stable mount for the eye globe which effectively isolates the cornea from the surrounding conjunctiva and enables measurements to be carried out on the corneal surface, free from contamination from mucin-producing elements of the conjunctiva.

Using the mounted corneas, four contact angle measurements were made to estabish whether adsorption of the polymer in an ophthalmic solution onto the cornea had occurred, and if so, to what extent the adsorbed polymer was retained.

The first measurement involved a reference contact angle which was made by determining the contact angle of a drop of saline (0.9 percent sodium chloride in distilled water) on the clear muci-free corneal surface. This measurement is reported below in Table III for all ophthalmic solution formulations under the column headed $C_1$.

A drop of each ophthalmic solution formulation was placed on the clean mucin-free corneal surface. The contact angle of this drop of the ophthalmic solution was measured and was reported below in Table III under the column headed $C_2$.

The cornea was then inverted and the corneal surface suspended in a given ophthalmic solution for 15 minutes as the solution was constantly stirred. Following the 15 minute adsorption period, the cornea was removed, dipped into saline to remove excess solution, and dried within the dust-free environment of a laminar and peripheral flow work station. Following drying (approximately 30 minutes) the contact angle of a drop of saline on the corneal surface which had been exposed to the polymer solution was measured. This angle is reported below in Table III under the column headed $C_3$.

After the determination of the contact angle of normal saline on the corneal surface which had been exposed to the polymer solution, the corneal mount was then positioned 2 mm beneath the opening of a buret and rinsed with normal saline for 60 seconds using a constant flow rate of 50 cc/60 sec. The contact angle of a drop of normal saline on the corneal surface was then measured. This value is reported below in Table III under the column headed $C_4$.

TABLE III

| Formulation No. | Contact Angle (degrees) | | | |
|---|---|---|---|---|
| | $C_1$ | $C_2$ | $C_3$ | $C_4$ |
| 1 | 48 | 39 | 43 | 50 |
| 2 | 49 | 52 | 61 | 67 |
| 3 | 51 | 29 | 18 | 20 |
| 4 | 48 | 41 | 25 | 24 |
| 5 | 48 | 17 | 20 | 20 |
| 6 | 48 | 27 | 23 | 25 |
| 7 | 48 | 30 | 20 | 20 |
| 8 | 53 | 31 | 15 | 35 |
| 9 | 50 | 43 | 18 | 16 |
| 10 | 47 | 49 | 31 | 65 |
| 11 | 47 | 46 | 30 | 30 |
| 12 | 51 | 42 | 31 | 42 |

Contact angle $C_1$ is a control. It represents the contact angle of normal saline on a clean corneal surface prior to any contact with an ophthalmic solution. This angle will vary 4°–5° depending on the particular rabbit cornea used. If any polymer is adsorbed on the corneal surface during the exposure period, then this will be reflected in the contact angle determined in columns $C_3$ and $C_4$ by a lower value of the contact angle than for the control contact angle.

Column $C_2$ represents the contact angle formed by a drop of the polymer solution on the corneal surface. A low value for this measurement indicates that the ophthalmic solution can have quick spreading properties. If the ophthalmic solution forms a large contact angle (45° or greater) there may be resistance to spreading or minor discomfort due to the eye lid having to mechanically spread the ophthalmic solution. Even more important is the fact that when dry areas or spots are present on the corneal surface, the ophthalmic solution must quickly spread to the dry spots or the solution may not be suitable for a dry eye tear substitute.

Reference to column $C_3$ indicates whether the ophthalmic solution has polymer adsorbed onto the corneal surface. The lower the value under $C_3$, the greater the indication of polymer adsorption.

The contact angle reported in column $C_4$ is the most critical measurement made. This is an indication of the resistivity to rinse-off or strength of adsorption of the polymer to the corneal surface. As described above, the corneas following the measurement shown in column $C_3$ were rinsed with saline to eliminate any polymer which was not adsorbed. If the polymer was completely rinsed from the surface of the cornea, the contact angle of a saline drop would change from the angle reported in column $C_3$ and return to the value reported in column $C_1$. If a higher value is found in column $C_4$ than in column $C_1$, the polymer may actually have disrupted the corneal surface. Those polymers which are strongly physically adsorbed are retained and the contact angle reported in column $C_4$ would be similar to the contact angle reported in column $C_3$.

As can be seen from an examination of the above tables, the formulations prepared in accordance with the present invention (Formulation Nos. 3-7), give low saline contact angles as reported in column $C_3$, and also have good retention of polymer as determined by the contact angle reported in column $C_4$. The values are as good or better than the values obtained with known prior art ophthalmic solutions. In addition, the ophthalmic solutions of the present invention have low intrinsic contact angles as reported in column $C_2$ indicating that the ophthalmic solutions of the invention are easily spread over the surface of the cornea.

EXAMPLE II

Artificial tear film solutions of the following compositions were prepared.

| Ingredient | Formulation No. 13 | Formulation No. 14 | Formulation No. 15 |
|---|---|---|---|
| Dextran 70 | 0.1% | 0.01% | 0.1% |
| Benzalkonium chloride | 0.01% | 0.01% | 0.01% |
| Disodium edetate | 0.05% | 0.05% | 0.05% |
| Sodium chloride | 0.58% | 0.77% | 0.77% |
| Potassium chloride | 0.075% | 0.12% | 0.12% |
| Calcium chloride | 0.048% | — | — |
| Magnesium chloride | 0.03% | — | — |
| Sodium acetate | 0.39% | — | — |
| Sodium citrate | 0.17% | — | — |
| Sodium hydroxide | qs pH 7.0 | qs pH 7.0 | qs pH 7.0 |
| Hydroxypropylmethylcellulose | — | — | 0.3% |
| Purified water | qs | qs | qs |

Each of the formulations was tested in humans to determine the tearfilm breakup time and the duration of the effect upon tearfilm breakup time caused by instillation of the formulation in the eye. The results of these tests are as follows:

| Formulation | Number of Patients | Tearfilm Stability | Duration |
|---|---|---|---|
| 13 | 4 | Negative Stabilizing | Effect 35–40 min. |
| 14 | 8 | Positive Stabilizing | Effect 90–100 min. |
| 15 | 8 | Positive Stabilizing | Effect 90–100 min. |

The negative tearfilm stabilizing effect of Formulation 13, containing divalent salts, resulted in a shorter tearfilm breakup time in the presence of the artificial tear solution than in its absence. The positive tearfilm stabiliing effect of Formulations 14 and 15, containing no divalent salts, results in an extended tearfilm breakup time.

Further, Formulations 14 and 15 exhibited improved tearfilm stability over a time period of 90–100 minutes whereas Formulation 13's effect was noticable for only 35–40 minutes. This indicates that the formulations which do not contain divalent cations are effective in stabilizing the tearfilm and at the same time are effectively retained on the cornea by adsorption.

What is claimed is:

1. An ophthalmic solution useful as an artificial tear comprising an aqueous solution of a polysaccharide selected from the group consisting of dextran and arabinogalactan, benzalkonium chloride, and water, said polysaccharide being present at a level of from about 0.001 to about 5 percent by weight and said benzalkonium chloride being present at a level of from about 0.001 to about 0.1 percent by weight.

2. An ophthalmic solution in accordance with claim 1 wherein said polysaccharide is dextran.

3. An ophthalmic solution in accordance with claim 2 wherein said dextran has a molecular weight in the range of from about 10,000 to about 1,000,000.

4. An ophthalmic solution in accordance with claim 1 wherein said polysaccharide is arabinogalactan.

5. An ophthalmic solution in accordance with claim 4 wherein said arabinogalactan has a molecular weight of from about 10,000 to about 250,000.

6. An ophthalmic solution in accordance with claim 1 which further comprises one or more monovalent cationic salts at a level sufficient to provide an isotonic solution.

7. An ophthalmic solution in accordance with claim 1 which further comprises a viscosity building agent.

8. An ophthalmic solution in accordance with claim 7 wherein said viscosity building agent is selected from the group consisting of natural gums, gelatin, starch derivatives, polymeric glycols, and cellulosic polymers.

* * * * *